United States Patent
Sabri

(10) Patent No.: US 10,046,770 B1
(45) Date of Patent: Aug. 14, 2018

(54) SYSTEMS AND METHODS FOR ESTIMATING A ROAD SURFACE FRICTION COEFFICIENT AND VEHICLE LATERAL VELOCITY USING A DECOUPLED DYNAMICAL MODEL

(71) Applicant: GM Global Technology Operations LLC, Detroit, MI (US)

(72) Inventor: Yadollah Sabri, Sterling Heights, MI (US)

(73) Assignee: GM GLOBAL TECHNOLOGY OPERATIONS LLC, Detroit, MI (US)

(*) Notice: Subject to any disclaimer, the term of this patent is extended or adjusted under 35 U.S.C. 154(b) by 0 days.

(21) Appl. No.: 15/482,977

(22) Filed: Apr. 10, 2017

(51) Int. Cl.
| | | |
|---|---|---|
| *A01B 69/00* | (2006.01) | |
| *B60W 40/068* | (2012.01) | |
| *B60W 10/20* | (2006.01) | |
| *B60W 10/18* | (2012.01) | |
| *B60W 10/04* | (2006.01) | |

(Continued)

(52) U.S. Cl.
CPC ........ *B60W 40/068* (2013.01); *B60W 10/04* (2013.01); *B60W 10/18* (2013.01); *B60W 10/20* (2013.01); *B60W 40/107* (2013.01); *B60W 40/109* (2013.01); *B60W 40/114* (2013.01); *B60W 2520/10* (2013.01); *B60W 2520/105* (2013.01); *B60W 2520/125* (2013.01); *B60W 2520/14* (2013.01); *B60W 2550/148* (2013.01); *B60W 2710/18* (2013.01); *B60W 2710/20* (2013.01); *B60W 2720/106* (2013.01)

(58) Field of Classification Search
CPC .... B60W 40/068; B60W 10/04; B60W 10/18; B60W 10/20; B60W 40/107; B60W 40/109; B60W 40/114; B60W 2520/10; B60W 2520/105; B60W 2520/125; B60W 2520/14; B60W 2550/148; B60W 2710/18; B60W 2710/20; B60W 2720/106
See application file for complete search history.

(56) References Cited

U.S. PATENT DOCUMENTS

| | | | | |
|---|---|---|---|---|
| 5,941,338 A | * | 8/1999 | Miller | ............... B62D 6/04 180/421 |
| 6,256,561 B1 | * | 7/2001 | Asanuma | ............... B62D 1/286 180/197 |

(Continued)

OTHER PUBLICATIONS

U.S. Appl. No. 15/440,348, filed Feb. 23, 2017, Adam et al.
U.S. Appl. No. 15/236,106, filed Aug. 12, 2016, Sabri et al.

*Primary Examiner* — Hussein Elchanti

(57) ABSTRACT

Systems and methods for independently estimating a road surface friction coefficient value and a vehicular lateral velocity value are provided. In one example, the system includes: a self-aligning torque coefficient estimating module configured to obtain sensor signals from an electronic power steering (EPS) system and an inertial measurement unit and estimate a first self-aligning torque coefficient value based on the sensor signals using a recursive least square algorithm; a road surface friction coefficient value estimating module configured to obtain the estimated first self-aligning torque coefficient value and estimate a first road surface friction coefficient value based on the estimated first self-aligning torque coefficient value; and a feature control module configured to generate one or more control signals configured to control features of a vehicle based on the estimated first road surface friction coefficient value.

20 Claims, 3 Drawing Sheets

(51) Int. Cl.
*B60W 40/107* (2012.01)
*B60W 40/109* (2012.01)
*B60W 40/114* (2012.01)

(56) References Cited

U.S. PATENT DOCUMENTS

| | | | |
|---|---|---|---|
| 6,675,928 B2 * | 1/2004 | Takai | B62D 5/065 180/422 |
| 9,463,827 B2 * | 10/2016 | Mose | B62D 5/0463 |
| 2002/0042671 A1 * | 4/2002 | Chen | B60K 28/16 701/41 |
| 2004/0204808 A1 * | 10/2004 | Satoh | B62D 6/005 701/41 |
| 2008/0078608 A1 * | 4/2008 | Hara | B62D 5/0484 180/446 |
| 2008/0091318 A1 * | 4/2008 | Deng | B62D 6/003 701/41 |
| 2011/0077824 A1 * | 3/2011 | Barton | B62D 6/005 701/42 |
| 2016/0101782 A1 | 4/2016 | Ghoneim et al. | |

* cited by examiner

SYSTEMS AND METHODS FOR ESTIMATING A ROAD SURFACE FRICTION COEFFICIENT AND VEHICLE LATERAL VELOCITY USING A DECOUPLED DYNAMICAL MODEL

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates generally to vehicles and, more particularly, to providing independent estimations of a road surface friction coefficient and lateral velocity of a vehicle.

The road surface friction coefficient ($\mu$) is used to characterize the slipperiness of a given road surface. For example, an icy road surface may be associated with a relatively low $\mu$ value, while a dry asphalt road surface may be associated with a relatively high $\mu$ value. Knowledge of the road surface friction coefficient has utility in a variety of vehicle applications. For example, a vehicle control system may use the road surface friction coefficient (or, more specifically, a reasonably accurate estimation of the road surface friction coefficient) to control one or more vehicle components in assisted, or autonomous, driving applications.

Additionally, it is desirable to know the lateral velocity of a vehicle. As with the road surface friction coefficient, a vehicle's control system may use the lateral velocity of a vehicle (or a reasonably accurate estimation of a vehicle's lateral velocity) to control one or more vehicle components in assisted, or autonomous, driving applications.

Traditionally, it was necessary to have an estimate of the road surface friction coefficient to estimate the lateral velocity of a vehicle, or to have an estimate of the lateral velocity to estimate the road surface friction coefficient. Stated differently, estimations of the road surface friction coefficient and vehicular lateral velocity were inextricably linked. Because of the intertwined nature of the road surface friction coefficient and vehicular lateral velocity, conventional systems were required to make assumptions to arrive at estimations for the road surface friction coefficient and lateral velocity, potentially compromising the accuracy of the estimations.

SUMMARY

Further areas of applicability of the present disclosure will become apparent from the detailed description, the claims and the drawings. The detailed description and specific examples are intended for purposes of illustration only and are not intended to limit the scope of the disclosure.

In a feature, a system for estimating a road surface friction coefficient value and/or vehicular lateral velocity value is provided. The system may include: a self-aligning torque coefficient estimating module; a road surface friction coefficient value estimating module operatively connected to the self-aligning torque coefficient estimating module; and a feature control module operatively connected to the road surface friction coefficient value estimating module. The self-aligning torque coefficient estimating module may be configured to obtain sensor signals from an electronic power steering (EPS) system and an inertial measurement unit (IMU) and estimate a first self-aligning torque coefficient value based on the sensor signals using a recursive least square algorithm. The road surface friction coefficient value estimating module may be configured to obtain the estimated first self-aligning torque coefficient value and estimate a first road surface friction coefficient value based on the estimated first self-aligning torque coefficient value. The feature control module may be configured to generate one or more control signals configured to control features of a vehicle based on the estimated first road surface friction coefficient value.

In further features, the system may include a lateral velocity estimating module operatively connected to the self-aligning torque coefficient estimating module. The lateral velocity estimating module may be configured to obtain the estimated first self-aligning torque coefficient value and estimate a first lateral velocity value based on the estimated first self-aligning torque coefficient value.

In further features, the feature control module may be further configured to generate the one or more control signals based on the estimated first lateral velocity.

In further features, the system may include a total EPS delivered torque value estimating module operatively connected to the self-aligning torque coefficient estimating module. The total EPS delivered torque value estimating module may be configured to estimate a first total EPS delivered torque value based on the estimated first self-aligning torque coefficient value.

In further features, the system may include an EPS diagnostic module operatively connected to the total EPS delivered torque value estimating module and the self-aligning torque coefficient estimating module. The EPS diagnostic module may be configured to determine whether the difference between the estimated first total EPS delivered torque value and the estimated first self-aligning torque coefficient value falls outside of a predetermined range.

In further features, the EPS diagnostic module may be configured to generate diagnostic results data in response to determining that the difference between the estimated first total EPS delivered torque value and the estimated first self-aligning torque coefficient value falls outside of the predetermined range. In further features, the diagnostic results data may include a diagnostic trouble code (DTC).

In further features, the self-aligning torque coefficient estimating module may be further configured to obtain different sensor signals from the EPS system and the IMU and estimate a second self-aligning torque coefficient value based on the different sensor signals using the recursive least square algorithm.

In further features, the road surface friction coefficient value estimating module may be further configured to obtain the estimated second self-aligning torque coefficient value and estimate a second road surface coefficient value based on the estimated second self-aligning torque coefficient value.

In further features, the road surface friction coefficient value estimating module may be further configured to estimate at least one of the first road surface coefficient value and the second road surface coefficient value in real-time (i.e., in a matter of milliseconds).

In further features, the lateral velocity estimating module may be further configured to obtain the estimated second self-aligning torque coefficient value and estimate a second lateral velocity value based on the estimated second self-aligning torque coefficient value.

In further features, the lateral velocity estimating module may be further configured to estimate at least one of the first lateral velocity value and the second lateral velocity value in real-time.

In further features, the total EPS delivered torque value estimating module is further configured to obtain the estimated second self-aligning torque coefficient value and estimate a second total EPS delivered torque value based on the estimated second self-aligning torque coefficient value.

In further features, the total EPS delivered torque value estimating module is further configured to estimate at least one of the first total EPS delivered torque value and the second total EPS delivered torque value in real-time.

In further features, the road surface friction coefficient value estimating module may be further configured to estimate the first road surface friction coefficient value independent of the estimated first lateral velocity value.

In further features, the lateral velocity estimating module may be further configured to estimate the first lateral velocity value independent of the estimated first road surface friction coefficient value.

In further features, the road surface friction coefficient value estimating module may be further configured to estimate the first road surface friction coefficient value under a plurality of different steering modes associated with a vehicle.

In further features, the road surface friction coefficient value estimating module may be further configured to estimate the first road surface friction coefficient value under a plurality of different slip angles associated with a vehicle.

In further features, the sensor signals may include at least some of the following dynamic variables of a vehicle: lateral acceleration; longitudinal acceleration; road wheel angle; yaw rate; longitudinal velocity; torsion bar torque; and EPS motor torque.

In further features, the control signals may be configured to control one or more of the following features of a vehicle: vehicle braking; vehicle steering; and vehicle acceleration.

In another feature, a method for estimating a road surface friction coefficient value and/or vehicular lateral velocity value is provided. The method may include: obtaining sensor signals from an EPS system and an IMU; estimating a first self-aligning torque coefficient value based on the sensor signals using a recursive least square algorithm; and estimating at least one of a first road surface friction coefficient value and a first lateral velocity value based on the estimated first self-aligning torque coefficient value.

In further features, the method may include generating one or more control signals configured to control features of a vehicle based on at least one of the estimated first road surface friction coefficient value and first lateral velocity value.

In further features, the method may include estimating a first total EPS delivered torque value based on the estimated first self-aligning torque coefficient value.

In further features, the method may include determining whether the difference between the estimated first total EPS delivered torque value and the estimated first self-aligning torque coefficient value falls outside of a predetermined range.

In further features, the method may include, responsive to determining that the difference between the estimated first total EPS delivered torque value and the estimated first self-aligning torque coefficient value falls outside of the predetermined range, generating diagnostic results data.

In further features, the method may include: obtaining different sensor signals from the EPS system and the IMU; estimating a second self-aligning torque coefficient value based on the different sensor signals using the recursive least square algorithm; and estimating at least one of a second road surface friction coefficient value and a second lateral velocity value based on the estimated second self-aligning torque coefficient value.

In further features, the method may include estimating a second total EPS delivered torque value based on the estimated second self-aligning torque coefficient value.

In further features, the method may include: determining whether the difference between the estimated second total EPS delivered torque value and the estimated second self-aligning torque coefficient value falls outside of a predetermined range; and responsive to determining that the difference between the estimated second total EPS delivered torque value and the estimated second self-aligning torque coefficient value falls outside of a predetermined range, generating diagnostic results data.

In further features, estimating the at least one of the first road surface friction coefficient value and the first lateral velocity value may include estimating the first road surface friction coefficient value and the first lateral velocity value independently of one another.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Figure 1:
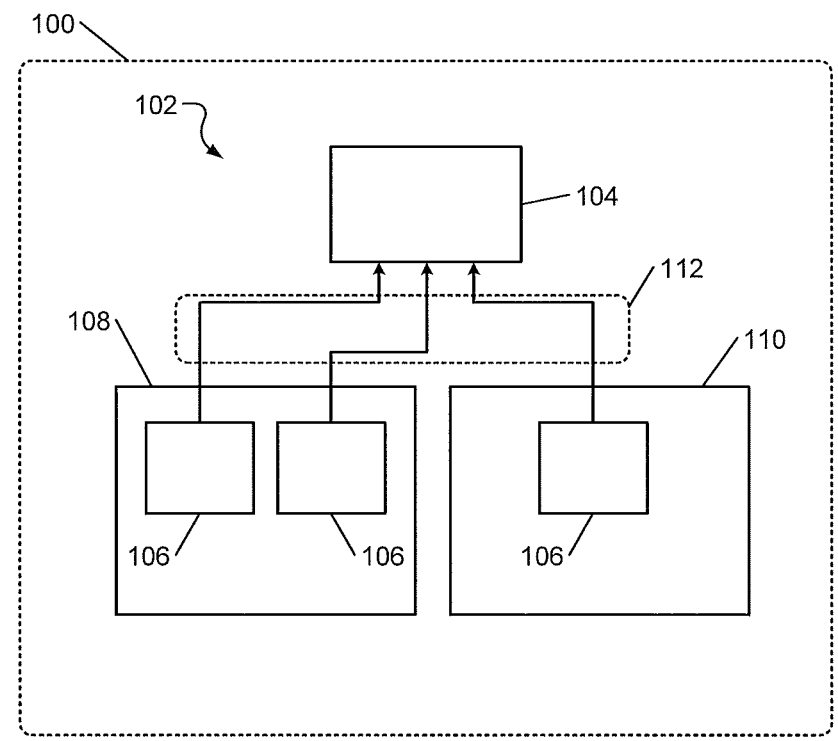
FIG. 1 is a functional block diagram of an example vehicle system.

Referring now to FIG. 1, an example vehicle 100 is shown. The vehicle 100 may be any type of vehicle that travels over a road surface, such as, but not limited to, an automobile. The vehicle 100 includes a control system 102. The control system 102 includes a control module 104, an electronic power steering (EPS) system 108, and an inertial measurement unit (IMU) 110. The EPS system 108 and IMU 110 may each be operatively connected (i.e., directly, or via one or more intervening elements) to the control module 104 via one or more wired or wireless communication channels.

The EPS system 108 includes one or more sensors 106. The one or more sensors 106 of the EPS system 108 are configured to sense observable conditions of the EPS system 108 and generate one or more sensor signals 112 based thereon. Similarly, the IMU 110 includes one or more sensors 106. The one or more sensors 106 of the IMU 110 are configured to sense observable conditions of the IMU 110 and generate one or more sensor signals 112 based thereon. The sensor signals may directly, or indirectly, convey dynamical parameters of the vehicle 100 including, but not limited to: torsion bar torque, EPS motor torque, yaw rate, longitudinal speed, longitudinal acceleration, lateral acceleration, road wheel angle, torsion bar angle, pneumatic trail, mechanical trail, and front slip stiffness coefficient.

The control module 104 obtains (i.e., receives or fetches) the sensor signals 112 and/or data captured by the sensors 106 and estimates a road surface friction coefficient (μ) reflecting the slipperiness of the road that the vehicle 100 is traveling upon. Additionally, or alternatively, the control module 104 utilizes the obtained sensor signals 112 and/or the data captured by the sensors 106 to estimate a lateral velocity of the vehicle. Further still, in some examples, the control module 104 utilizes the obtained sensor signals 112 and/or data captured by the sensors 106 to estimate a total EPS delivered torque ($T_{EPS}$) value. As discussed in additional detail below, the total EPS delivered torque value may be utilized in some examples to perform a diagnostic check on the health condition of the vehicle's 100 EPS system 108.

Figure 2:
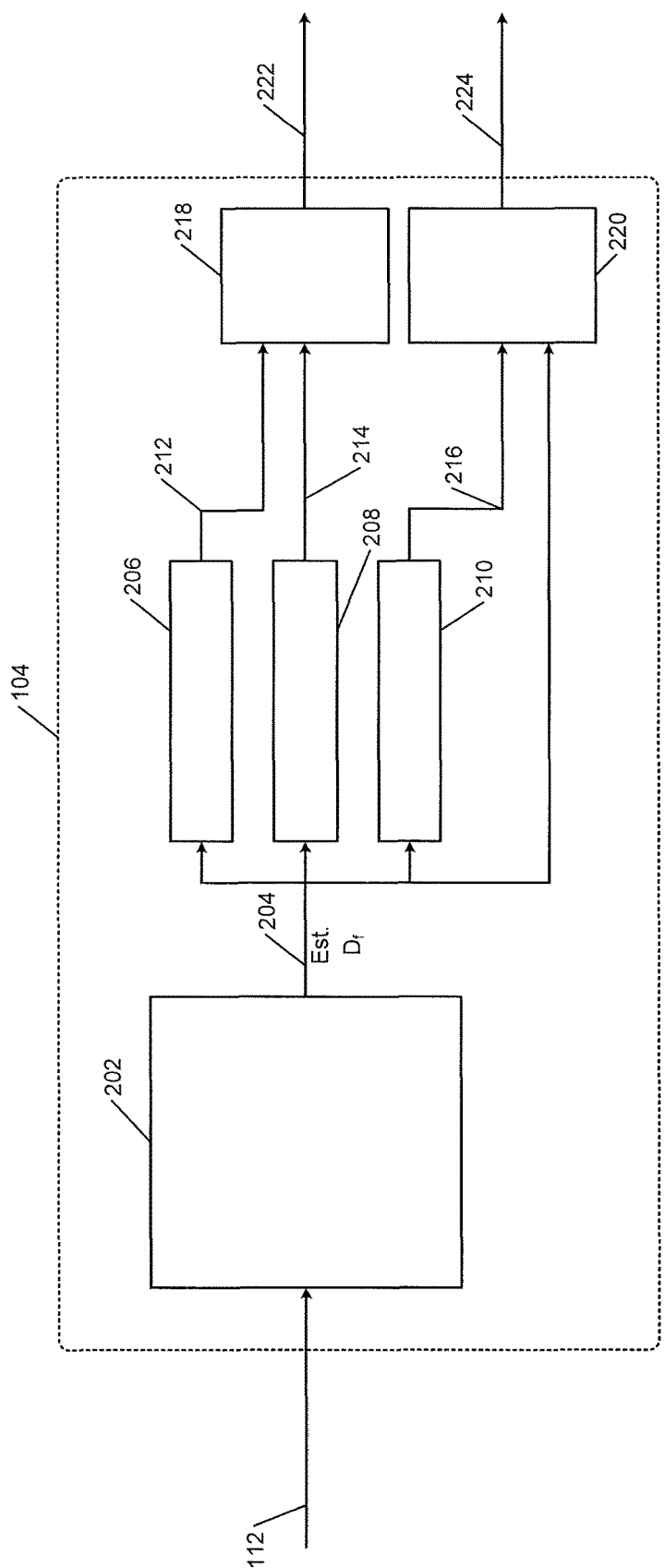
FIG. 2 is a functional block diagram of an example implementation of a vehicle control module.

Referring now to FIG. 2, and with continued reference to FIG. 1, a functional block diagram of an example implementation of the control module 104 is shown. In the example implementation of FIG. 2, the control module 104 includes a self-aligning torque coefficient ($D_f$) estimating module 202, a road surface friction coefficient (μ) estimating module 206, a lateral velocity ($V_y$) estimating module 208, and a total EPS delivered torque ($T_{EPS}$) estimating module 210. In addition, in some examples, the control module 104 includes a feature control module 218 and/or an EPS diagnostic module 220.

In operation, the self-aligning torque coefficient ($D_f$) estimating module 202 obtains the sensor signals 112 from the sensors 106 of the EPS System 108 and IMU 110. The self-aligning torque coefficient ($D_f$) estimating module 202 calculates an estimated self-aligning torque coefficient ($D_f$) value 204 based on the sensor signals 112. In one example, the self-aligning torque coefficient ($D_f$) estimating module 202 calculates the estimated self-aligning torque coefficient ($D_f$) value 204 based on the sensor signals 112 by utilizing a recursive least square (RLS) algorithm according to the following discussion.

The relationships between the self-aligning torque coefficient ($D_f$) value, road surface friction coefficient (μ) value, lateral velocity ($V_y$) value, and total EPS delivered torque ($T_{EPS}$) value may be expressed according to the following EPS decoupled dynamical model:

$$T_{EPS} = 2D_f \left( \delta - \overbrace{\frac{v_y + aY_r}{V_x}}^{Slip\_Angle} \right) \quad (1)$$

$$v_y = V_x \left( \delta - \frac{T_{EPS}}{2D_f} \right) - aY_r \quad (2)$$

$$a_y = \dot{v}_y + Y_r \cdot V_x \quad (3)$$

$$\dot{T}_{EPS} = 2D_f \left[ \dot{\delta} - \frac{V_x(\dot{v}_y + a\dot{Y}_r) - \dot{V}_x(v_y + aY_r)}{V_x^2} \right] \quad (4)$$

$$\frac{\dot{T}_{EPS}}{2} + \frac{\dot{V}_x}{2V_x} T_{EPS} = D_f \left( \dot{\delta} + Y_r - \frac{a_y + a\dot{Y}_r - \dot{V}_x \delta}{V_x} \right) \quad (5)$$

$$D_f = \mu(t_m + t_p) \cdot C_f \quad (6)$$

where δ is the road wheel angle (Rad), $Y_r$ is the yaw rate (Rad/s), $V_y$ is the lateral velocity (m/s), $V_x$ is the longitudinal speed (m/s), $D_f$ is the self-aligning torque coefficient (Nm/Rd), μ is the road surface friction coefficient, $t_p$ is the pneumatic trail (m), $t_m$ is the mechanical trail (m), $T_{EPS}$ is the total EPS delivered torque (Nm), $C_f$ is the front slip stiffness coefficient, and $a_y$ is the lateral acceleration (m/s^2).

As shown, the self-aligning torque coefficient ($D_f$) value is related to road surface friction coefficient (μ) value according to equation (6) above. The foregoing approach may be utilized to provide an estimation of the road surface friction coefficient (μ) value under a myriad of vehicle operation modes including, but not limited to, (1) fast, moderate, or slow steering modes and/or (2) any slip angles, ranging from from very small to very large.

The self-aligning torque coefficient ($D_f$) estimating module 202 is configured to apply a RLS algorithm to provide real-time (i.e., in a matter of milliseconds) estimations of the self-aligning torque coefficient ($D_f$) (and, consequently, real-time estimations of μ, $V_y$, and $T_{EPS}$) based on the decoupled estimator extracted from the EPS decoupled dynamical model and vehicle dynamics as illustrated by equation (5) and the following additional equations:

$$\hat{d}(n) = a \cdot x_1(n) + bx_2(n) \quad (7)$$

$$OR: \hat{d}(n) = \theta' \cdot x \quad (8)$$

$$\theta = [a \ b]'; x = [x_1 \ x_2]$$

$$a = D_f; x_1 = \dot{\delta} + Y_r - \frac{a_y + a\dot{Y}_r - \dot{V}_x \delta}{V_x}; x_2 = 1;$$

$$d = \frac{\dot{T}_{EPS}}{2} + \frac{\dot{V}_x}{2V_x} T_{EPS}$$

Applying the RLS algorithm, the self-aligning torque coefficient ($D_f$) estimating module 202 updates the above-mentioned parameters a and b upon arrivals of each new d(i) and x(i) samples (representing newly obtained values of sensor signals 112).

The RLS algorithm is an adaptive filter which recursively finds coefficients that minimize a weighted linear least squares cost function relating to input signals. The goal of a RLS filter is to minimize a cost function C by appropriately selecting the filter coefficients $W_n$, updating the filter as new data arrives (e.g., newly obtained sensor signals 112). The error signal e(n) and desired signal d(n) are defined by the following equations:

$$e(n) = d(n) - X'(n)w(n-1) \quad (9)$$

$$g(n) = P(n-1)X(n)\{\lambda + X'(n)P(n-1)X(n)\}^{-1}$$

$$P(n) = \lambda^{-1}P(n-1) - g(n)X'(n)\lambda^{-1}P(n-1)$$

$$w(n) = w(n-1) + e(n)g(n)$$

Applying the foregoing RLS technique, the self-aligning torque coefficient ($D_f$) estimating module 202 may recursively provide a $D_f$ estimate 204 in substantially real-time based on newly obtained sensor signals 112, which real-time $D_f$ estimate 204 may be used to provide real-time estimates of μ, $V_y$, and $T_{EPS}$ values, as discussed below.

Returning to FIG. 2, the estimated self-aligning torque coefficient ($D_f$) value 204 may serve as input into the road surface friction coefficient (μ) estimating module 206, lateral velocity ($V_y$) estimating module 208, total EPS delivered torque ($T_{EPS}$) estimating module 210, and, in some examples, the EPS diagnostic module 220.

The road surface friction coefficient (μ) estimating module 206 is configured to determine an estimated road surface friction coefficient (μ) value 212 based on the estimated self-aligning torque coefficient ($D_f$) value 204. More specifically, the road surface friction coefficient (μ) estimating module 206 is configured to determine the estimated road surface friction coefficient (μ) value 212 according to the following equation:

$$\mu = D_f / D_{f0} \tag{10}$$

where $D_f$ is the estimated self-aligning torque coefficient value 204 and $D_{f0}$ is a referential self-aligning torque coefficient value.

In one example, $D_{f0}$ is a predetermined value designed to reflect a typical self-aligning torque coefficient value under standard driving conditions (e.g., a dry asphalt road under moderate steering mode). Applying the foregoing technique allows for the determination of a quantitative representation of the road surface friction coefficient (μ), which may be used to, among other things, adjust controls of the vehicle to provide an improved driving experience. In some examples, the road surface friction coefficient (μ) value may be between 0 and 1, where typical values are 0.1 for ice, 0.35 for snow, and 1.0 for dry road surface conditions.

The lateral velocity ($V_Y$) estimating module 208 is configured to determine an estimated lateral velocity ($V_Y$) value 214 based on the estimated self-aligning torque coefficient ($D_f$) value 204. More specifically, the lateral velocity ($V_Y$) estimating module 208 is configured to determine the estimated lateral velocity ($V_Y$) value 214 according to equation (2) above.

In one example, the control module 104 additionally includes a feature control module 218. The feature control module 218 is configured to accept as input the estimated road surface friction coefficient (μ) value 212 and/or estimated lateral velocity ($V_Y$) value 214 and generate control signals 222 based thereon. More specifically, the feature control module 218 is configured to generate control signals 222 configured to control one or more features of the vehicle 100. By way of example and not limitation, the control signals 222 may be configured to effectuate the following vehicular actions: autonomous or driver-assisted braking, steering, and/or acceleration; generating a driver alert regarding the slipperiness of the road surface; generating an alert regarding the slipperiness of the road surface for transmission over one or more wireless communication channels to other drivers; or any other suitable vehicular actions known in the art.

The total EPS delivered torque ($T_{EPS}$) estimating module 210 is configured to determine an estimated total EPS delivered torque ($T_{EPS}$) value 216 based on the estimated self-aligning torque coefficient ($D_f$) value 204. More specifically, the total EPS delivered torque ($T_{EPS}$) estimating module 210 is configured to determine the estimated total EPS delivered torque ($T_{EPS}$) value 216 according to equation (1) above.

In one example, the control module 104 additionally includes an EPS Diagnostic Module 220. The EPS Diagnostic Module 220 is configured to accept as input the total EPS delivered torque ($T_{EPS}$) value 216 and the estimated self-aligning torque coefficient ($D_f$) value 204 and generate diagnostic results data 224 based thereon. More specifically, the EPS diagnostic module 220 is configured to generate diagnostic results data 224 representative of a health condition of the vehicle's 100 EPS system 108.

In one example, the EPS diagnostic module 220 is configured to assess the health of the vehicle's 100 EPS system 108 by comparing an estimated self-aligning torque coefficient ($D_f$) value 204 with an estimated total EPS delivered torque ($T_{EPS}$) value 216, and determining whether the difference between the estimated self-aligning torque coefficient ($D_f$) value 204 and the estimated total EPS delivered torque ($T_{EPS}$) value 216 falls outside of a predetermined range.

In one example, the diagnostic results data 224 may include data indicating that the vehicle's 100 EPS system 108 is in good health (i.e., functioning properly within prescribed limits). In another example, the diagnostic results data 224 may include data indicating that the vehicle's 100 EPS system 108 is in poor health (i.e., not functioning properly or within prescribed limits). In one example, the EPS diagnostic module 220 is configured to generate diagnostic results data 224 in the form of a diagnostic trouble code (DTC) when it is determined that the difference between the estimated self-aligning torque coefficient ($D_f$) value 204 and the estimated total EPS delivered torque ($T_{EPS}$) value 216 falls outside of a predetermined range.

Figure 3:
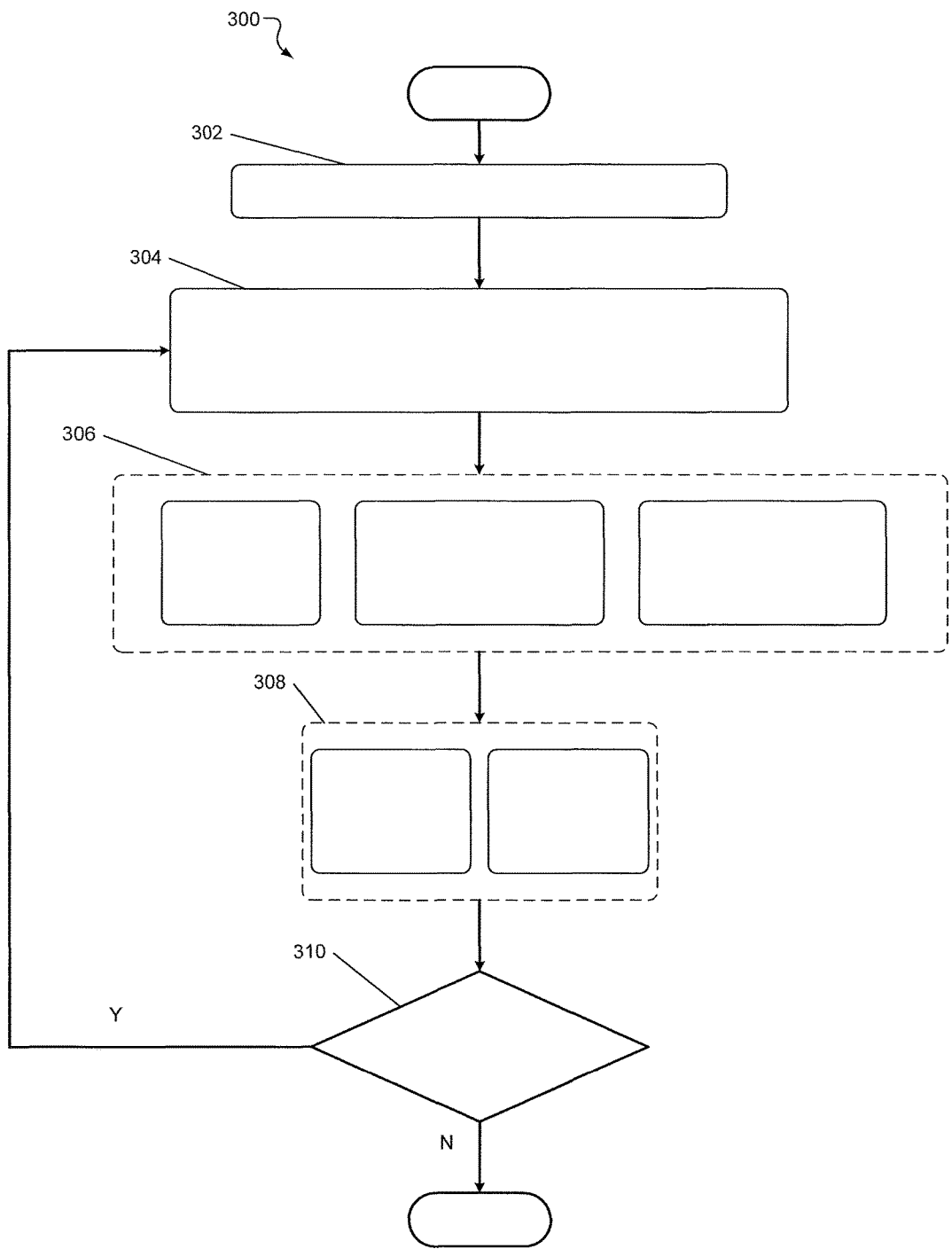
FIG. 3 is a flowchart illustrating an example method for estimating a road surface friction coefficient value, vehicular lateral velocity value, and/or total EPS delivered torque value.

Referring now to FIG. 3, a flowchart illustrating an example method 300 of estimating a road surface friction coefficient value, vehicular lateral velocity value, and/or total EPS delivered torque value is provided. The method 300 beings at 302 where sensor signals are obtained from, for example, an EPS system and/or IMU of a vehicle. At 304, an estimated self-aligning torque coefficient ($D_f$) value is determined using a RLS algorithm in accordance with the process for estimating a self-aligning torque coefficient ($D_f$) value using a RLS algorithm set forth above in this disclosure.

At 306, one or more of a road surface friction coefficient (μ) value, lateral velocity value ($V_Y$), and/or total EPS delivered torque ($T_{EPS}$) value are estimated based on the estimated self-aligning torque coefficient ($D_f$) value in accordance with the processes for estimating the road surface friction coefficient (μ) value, lateral velocity ($V_Y$) value, and/or total EPS delivered torque ($T_{EPS}$) value set forth above in this disclosure. In one example, the road surface friction coefficient (μ) value, lateral velocity ($V_Y$) value, and/or total EPS delivered torque ($T_{EPS}$) value are estimated substantially contemporaneously. In another example, the road surface friction coefficient (μ) value, lateral velocity value ($V_Y$), and/or total EPS delivered torque ($T_{EPS}$) value are estimated at different times.

At 308, a vehicle may be controlled based on control signals. The control signals may be generated based on the estimated road surface friction coefficient (μ) value and/or lateral velocity ($V_Y$) value. Additionally, or alternatively, at 308, diagnostics results data may be generated. In one example, the vehicle control and the diagnostics results data generation are carried out substantially contemporaneously. In another example, the vehicle control and the diagnostics results data generation are carried out at different times.

At 310, it is determined whether new sensor signals have been obtained. This may include, for example, obtaining sensor signals (e.g., from one or more sensors included as part of a vehicle's EPS system and/or IMU) periodically. In one example, new sensor signals are obtained substantially in real-time. If, at 312, new sensor signals have been obtained, the method returns to 304 where a new estimated self-aligning torque coefficient ($D_f$) value is determined based on the newly obtained sensor signals. Based on the new estimated self-aligning torque coefficient ($D_f$) value, new estimations for a road surface friction coefficient (μ) value, a lateral velocity ($V_Y$) value, and a total EPS delivered torque ($T_{EPS}$) value may be determined. If, at 310, new sensor signals have not been obtained, the method ends.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP:

Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A system comprising:
a self-aligning torque coefficient estimating module configured to:
   obtain sensor signals from an electronic power steering (EPS) system and an inertial measurement unit; and
   estimate a first self-aligning torque coefficient value based on the sensor signals using a recursive least square algorithm;
a road surface friction coefficient value estimating module configured to:
   obtain the estimated first self-aligning torque coefficient value; and
   estimate a first road surface friction coefficient value based on the estimated first self-aligning torque coefficient value; and
a feature control module configured to:
generate one or more control signals configured to control features of a vehicle based on the estimated first road surface friction coefficient value.

2. The system of claim 1, further comprising:
a lateral velocity estimating module configured to:
   obtain the estimated first self-aligning torque coefficient value; and
   estimate a first lateral velocity value based on the estimated first self-aligning torque coefficient value.

3. The system of claim 2, wherein the feature control module is further configured to generate the one or more control signals based on the estimated first lateral velocity.

4. The system of claim 1, further comprising:
a total EPS delivered torque value estimating module configured to:
   estimate a first total EPS delivered torque value based on the estimated first self-aligning torque coefficient value.

5. The system of claim 4, further comprising:
an EPS diagnostic module configured to:
   determine whether the difference between the estimated first total EPS delivered torque value and the estimated first self-aligning torque coefficient value falls outside of a predetermined range.

6. The system of claim 5, wherein the EPS diagnostic module is further configured to:
   generate diagnostic results data in response to determining that the difference between the estimated first total EPS delivered torque value and the estimated first self-aligning torque coefficient value falls outside of the predetermined range.

7. The system of claim 6, wherein the diagnostic results data comprises a diagnostic trouble code (DTC).

8. The system of claim 1, wherein the self-aligning torque coefficient estimating module is further configured to:
   obtain different sensor signals from the electronic power steering system and the inertial measurement unit; and
   estimate a second self-aligning torque coefficient value based on the different sensor signals using the recursive least square algorithm.

9. The system of claim 8, wherein the road surface friction coefficient value estimating module is further configured to:
   obtain the estimated second self-aligning torque coefficient value; and
   estimate a second road surface coefficient value based on the estimated second self-aligning torque coefficient value.

10. The system of claim 9, wherein the road surface friction coefficient value estimating module is further configured to:
   estimate at least one of the first road surface coefficient value and the second road surface coefficient value in real-time.

11. The system of claim 2, wherein the self-aligning torque coefficient estimating module is further configured to:
   obtain different sensor signals from the electronic power steering system and the inertial measurement unit; and
   estimate a second self-aligning torque coefficient value based on the different sensor signals using the recursive least square algorithm; and
   wherein the lateral velocity estimating module is further configured to:
      obtain the estimated second self-aligning torque coefficient value; and
      estimate a second lateral velocity value based on the estimated second self-aligning torque coefficient value.

12. The system of claim 11, wherein the lateral velocity estimating module is further configured to:
   estimate at least one of the first lateral velocity value and the second lateral velocity value in real-time.

13. The system of claim 4, wherein the self-aligning torque coefficient estimating module is further configured to:
   obtain different sensor signals from the electronic power steering system and the inertial measurement unit; and
   estimate a second self-aligning torque coefficient value based on the different sensor signals using the recursive least square algorithm; and
   wherein the total EPS delivered torque value estimating module is further configured to:
      obtain the estimated second self-aligning torque coefficient value; and
      estimate a second total EPS delivered torque value based on the estimated second self-aligning torque coefficient value.

14. The system of claim 13, wherein the self-aligning torque coefficient estimating module is further configured to:
   estimate at least one of the first total EPS delivered torque value and the second total EPS delivered torque value in real-time.

15. The system of claim 1, wherein the road surface friction coefficient value estimating module is further configured to:
   estimate the first road surface friction coefficient value independent of a lateral velocity value.

16. The system of claim 2, wherein the lateral velocity estimating module is further configured to:
   estimate the first lateral velocity value independent of the estimated first road surface friction coefficient value.

17. The system of claim 1, wherein the road surface friction coefficient value estimating module is further configured to:
   estimate the first road surface friction coefficient value under a plurality of different steering modes associated with a vehicle.

18. The system of claim 1, wherein the road surface friction coefficient value estimating module is further configured to:

estimate the first road surface friction coefficient value under a plurality of different slip angles associated with a vehicle.

19. The system of claim 1, wherein the sensor signals comprise at least some of the following dynamic variables of a vehicle:
   lateral acceleration;
   longitudinal acceleration;
   road wheel angle;
   yaw rate;
   longitudinal velocity;
   torsion bar torque; and
   EPS motor torque.

20. The system of claim 1, wherein the control signals are configured to control at least one of the following features of a vehicle:
   vehicle braking;
   vehicle steering; and
   vehicle acceleration.

* * * * *